United States Patent
Hörth

[11] Patent Number: 6,129,244
[45] Date of Patent: Oct. 10, 2000

[54] DEVICE FOR DISPENSING A MIXED DENTAL MULTICONSTITUENT MASS

[75] Inventor: Hans Hörth, Hamburg, Germany

[73] Assignee: Ernst Muhlbauer KG, Hamburg, Germany

[21] Appl. No.: 09/194,534

[22] PCT Filed: Apr. 6, 1998

[86] PCT No.: PCT/EP98/01993

§ 371 Date: Nov. 25, 1998

§ 102(e) Date: Nov. 25, 1998

[87] PCT Pub. No.: WO98/44860

PCT Pub. Date: Oct. 15, 1998

[30] Foreign Application Priority Data

Apr. 8, 1997 [DE] Germany ............ 297 06 235 U

[51] Int. Cl.⁷ ................................ B65D 35/22
[52] U.S. Cl. ................ 222/94; 222/105; 222/326; 222/386
[58] Field of Search ................... 222/74, 105, 326, 222/386

[56] References Cited

U.S. PATENT DOCUMENTS

| | | |
|---|---|---|
| 3,782,600 | 1/1974 | Columbus ............................. 222/94 |
| 4,099,651 | 7/1978 | Von Winckelmann .................... 222/94 |
| 4,652,175 | 3/1987 | Mauthe .................... 405/260 |
| 4,838,457 | 6/1989 | Swahl et al. ............... 222/94 |
| 5,137,178 | 8/1992 | Stokes et al. ............. 222/94 |
| 5,330,079 | 7/1994 | Keller ..................... 222/326 |
| 5,332,122 | 7/1994 | Herold et al. ............ 222/105 |
| 5,419,460 | 5/1995 | Herold et al. ............ 222/105 |
| 5,697,524 | 12/1997 | Sedlmeir .................. 222/94 |

FOREIGN PATENT DOCUMENTS

| | | |
|---|---|---|
| 319666 | 6/1989 | European Pat. Off. . |
| 9412703 | 10/1994 | Germany . |

*Primary Examiner*—Kevin Shaver
*Assistant Examiner*—David Deal
*Attorney, Agent, or Firm*—Alix, Yale & Ristas, LLP

[57] ABSTRACT

Arrangement for dispensing a mixed dental multi-component composition, with tubular bags (5, 6) which contain the components of the composition that are to be mixed, and with a unit for pressing the components out. This unit has a head piece (9), with channels (38, 39) for guiding the pressed-out components to attachments (10, 11) provided on the head piece (9), and with a mixer (15) which can be attached thereto. According to the invention, the head piece (9) including the attachments (10, 11) is firmly connected to the tubular bags (5, 6) and can be exchanged along with these.

5 Claims, 3 Drawing Sheets

DEVICE FOR DISPENSING A MIXED DENTAL MULTICONSTITUENT MASS

CROSS-REFERENCE TO RELATED APPLICATIONS

This is the national stage of International Application No. PCT/EP98/01993 filed Apr. 6, 1998.

BACKGROUND OF THE INVENTION

For dental impression compositions, two-component compositions are used which are contained in tubular bags. These bags are held in a cylinder inside a dispensing unit. The composition is pressed out by the action of a plunger and dispensed through a mixer (EP-A 492 413). In a known unit of this type (EP-A 541 972), each tubular bag is provided at its front end with a mouthpiece which cooperates sealingly with a complementary opening on the end face of the cylinder. The end face of the cylinder forms a head piece in which there are channels for guiding the components to attachment pieces to which the mixer can be connected. The cylinders and the head piece are fixed elements of the dispensing unit. If one wishes to exchange the bags containing the components, then the bags are removed from the cylinders holding them, and other bags are inserted, during which procedure care has to be taken to ensure that their mouthpieces have a sealed connection to the openings provided in the head piece. It can easily happen that the sealed connection is not obtained, or is not obtained directly upon insertion, and that some of the components pass into the unit. It can also happen that air is trapped in the composition and leads to errors during use, or that components are erroneously mixed up.

SUMMARY OF THE INVENTION

These disadvantages are avoided by the invention by virtue of the fact that the head piece, including the attachments for the mixer, is firmly connected to the tubular bags and can be exchanged along with these. The head piece is expediently bonded sealingly to the end face of the associated bag or bags. It is also expedient if a single head piece containing a plurality of separate channels is connected to a plurality of associated tubular bags. However, the invention also covers those embodiments in which a separate head piece is provided for each tubular bag.

The head piece can be designed as one single piece. In this case, the bag, after its pigtail closure has been opened, is connected, for example adhesively bonded, to the head piece. The arrangement can also be such that the bag is provided with a closure which opens under excess pressure. In this case it is possible to connect the closed tube to the head piece and to leave the opening process to the pressure which arises on account of the plunger movement when using the unit. A design is preferred in which the head piece consists of at least two parts, of which one can be connected to at least one tubular bag in such a way that the closure end or pigtail closure of the latter is accessible and can be opened from that side of this part directed away from the bag as long as this part of the head piece has not yet been connected to the other parts of the head piece.

BRIEF DESCRIPTION OF THE INVENTION

The invention is explained in greater detail below with reference to the drawing, which illustrates an advantageous embodiment and in which.

DESCRIPTION OF A PREFERRED EMBODIMENT

Figure 1:
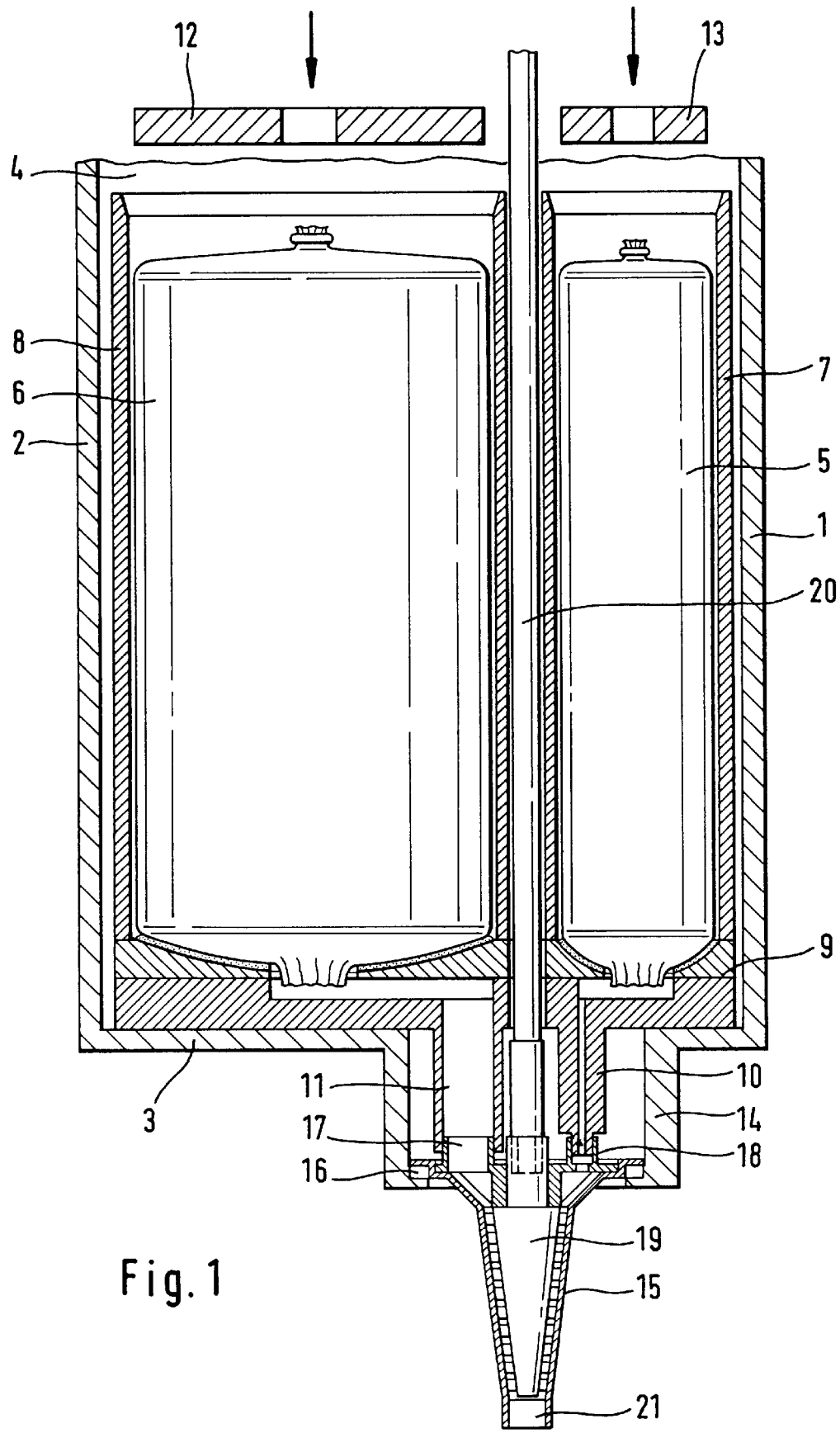
FIG. 1 shows a longitudinal section through the arrangement.

A dispensing unit whose housing is indicated by the walls 1, 2, 3 forms a receiving space 4 for free-flowing components contained in tubular bags 5, 6. The tubular bags 5, 6 are supported by cylinders 7, 8. In addition, the tubular bags are firmly connected to a head piece 9 which forms attachment pieces 10, 11 through which the components pressed out from the tubular bags 5, 6 by means of plungers 12, 13 can exit. Provided on the end wall 3 of the dispensing unit there is a holder 14 in which the attachment pieces 10, 11 are situated and on which a mixer 15 can be secured, for example by means of a bayonet closure 16, in such a way that its attachment pieces 17, 18 are connected sealingly to the attachment pieces 10, 11. The mixer 15 can be a static or dynamic mixer of known design. If it is a dynamic mixer, its shaft 19 is coupled to a drive shaft 20 of the dispensing unit. The components pressed out from the bags 5, 6 pass through the mixer 15 together and exit its nozzle 21 in a thoroughly mixed state. The composition in question here is, for example, a dental impression composition. To this extent the arrangement can be regarded as being known.

The tubular bags 5, 6 containing the components that are to be mixed are originally closed at both ends so as to form in each case a pigtail closure 25, 26 and 27, 28. The front end of each bag is bonded to a concavely adapted surface 30, 31 by means of a sealing adhesive composition 29, this surface 30, 31 being formed on the rear part 32 of the head piece 9. It surrounds an opening 33, 34 through which the pigtail closure 27, 28 penetrates or is at least accessible, as long as this part 32 has not yet been connected to the other part 35 of the head piece.

The parts 32, 35 of the head piece 9 have surfaces 36, 37 which are bonded sealingly to one another in such a way that the openings 33, 34 are closed off completely from the atmosphere and from each other. Formed within each of the two closed-off areas of the join, there is a channel 38, 39 which in each case leads from an opening 33, 34 to the associated attachment piece 10 or 11. In the storage state, these attachment pieces can be sealed off by means of a twin closure stopper 40. After insertion into the unit, the stopper 40 is replaced by the mixer 15.

For connecting the head piece 9 to the bags 5, 6, the procedure is that first the part 32 of the head piece is bonded to the bags, and the pigtail closures 28, 29 are opened, for example cut off. Thereafter, the two parts 32, 35 of the head piece 9 are bonded or welded sealingly to one another.

Figure 3:
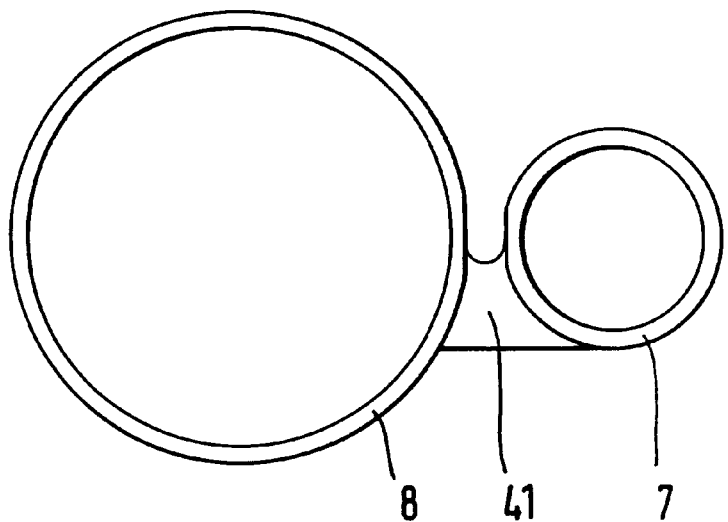
FIGS. 2 and 3 show a side view and an end view of the cylinders.
Figure 2:
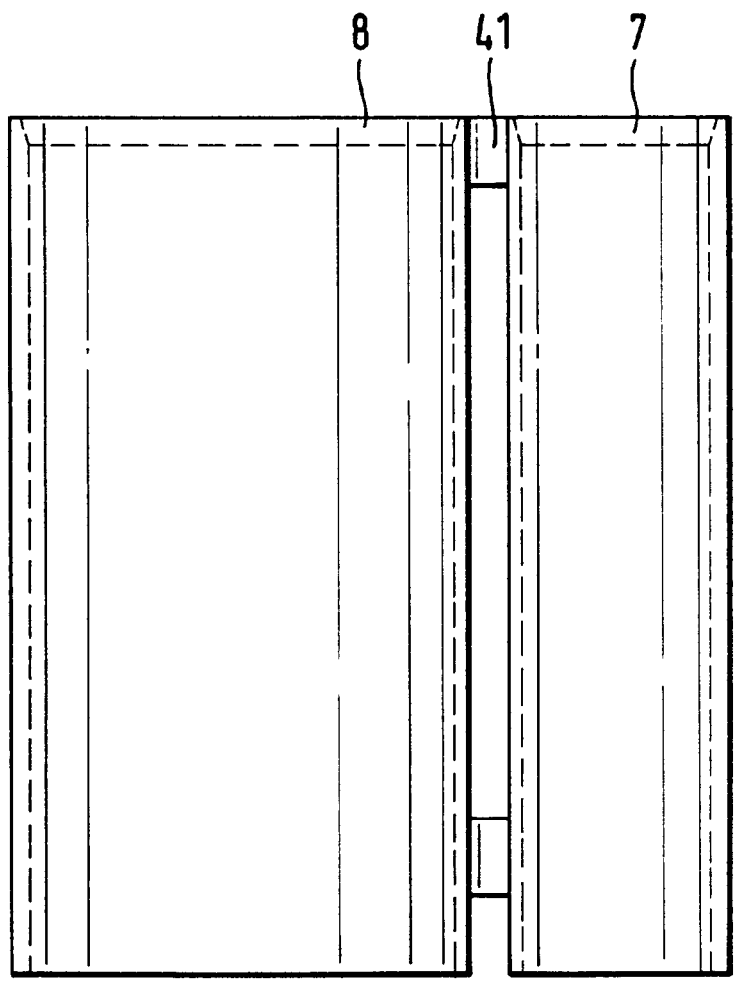
Figure 5:
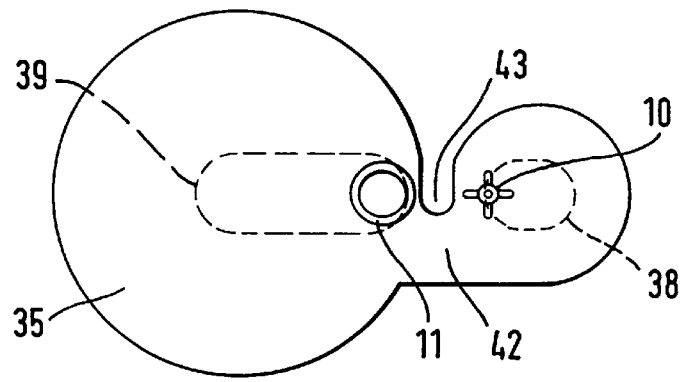
FIGS. 4 and 5 show a side view and an end view of the tubular bags connected to the head piece.
Figure 4:
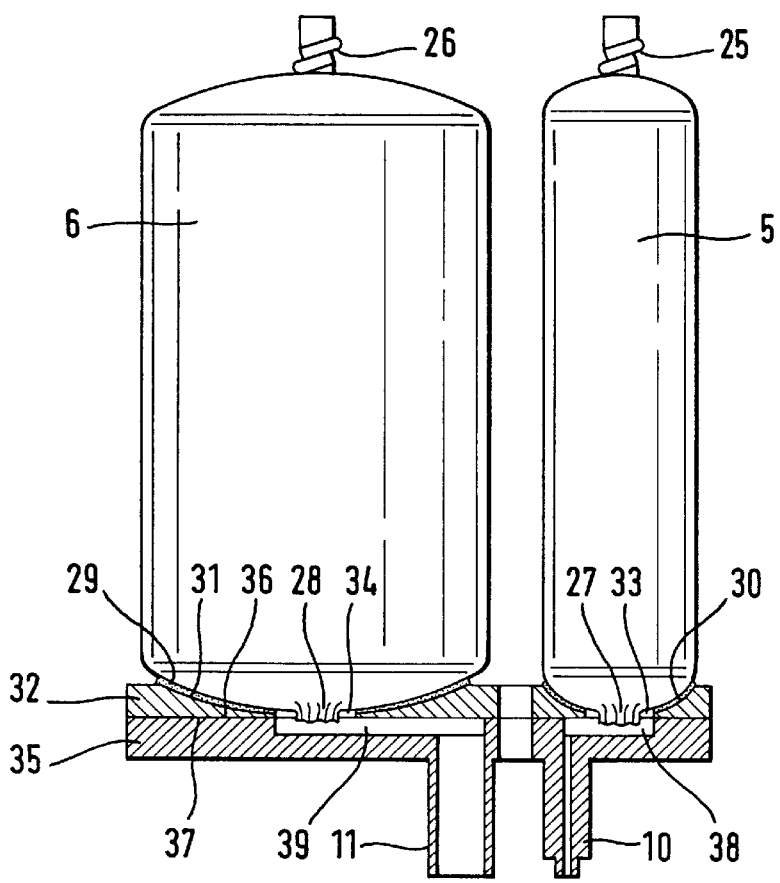
Figure 6:
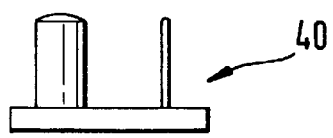
FIG. 6 shows a stopper for the attachment pieces of the head piece.

The cylinders 7, 8 can be firmly connected to the head piece 9. In general it is more appropriate and less expensive for them to be provided, as shown in FIGS. 2 and 3, as separate parts that can be exchanged and reused. To simplify use, they can be connected rigidly to one another by bridges 41. Their contour matches that of the head piece 9.

In the manner illustrated in the drawing, the central part 42 of the head piece 9 can, like the bridges 41, be arranged slightly off-centre so that the area 43 in the middle between the attachment pieces 10, 11 is open towards the side opposite the bridge 41, 42. In this way it is possible for the insert consisting of the bags 11, 12, the cylinders 28, 29 and the head piece 9 to be introduced from one side, generally from the upper side, into the dispensing unit, in which case the opening 43 receives an optionally present mixer shaft 20 centrally with respect to the attachment pieces 10, 11.

The invention eliminates any sealing problems between the tubular bags and the head piece during use. Moreover, associated components connected to the same head piece can no longer be erroneously mixed up. The replacement procedure is a very simple one.

What is claimed is:

1. Arrangement for dispensing a mixed dental multi-component composition, with tubular bags which contain the components of the composition, with a unit for pressing the components out, with a head piece with channels for guiding the pressed-out components to attachments provided on the head piece, and with a mixer which can be attached thereto, characterized in that the head piece including the attachments is firmly connected to the tubular bags and is exchanged along with the tubular bags.

2. Arrangement according to claim 1, characterized in that the head piece is bonded sealingly to a closure end of the bags through which the components will pass.

3. The arrangement according to claim 2, wherein said head piece comprises a first part and a second part, said first part connected to at least one tubular bag whereby the closure end of the tubular bag is accessible from a side of said first part opposite said connection prior to the assembly of said first part to said second part.

4. The arrangement of claim 3, wherein said closure end is removed, said first part is connected to said second part and a stopper is inserted into said attachments, said stopper sealing said attachments and said channels from the ambient atmosphere.

5. Arrangement according to claim 1, characterized in that a single head piece containing a plurality of separate channels is connected to a plurality of tubular bags.

* * * * *